(12) United States Patent
Schmid (10) Patent No.: US 9,149,510 B2
(45) Date of Patent: *Oct. 6, 2015

(54) COMBINATIONS OF SOMATOSTATIN-ANALOGS WITH DIFFERENT SELECTIVITY FOR HUMAN SOMATOSTATIN RECEPTOR SUBTYPES

(71) Applicant: Herbert Schmid, Neuenburg (DE)

(72) Inventor: Herbert Schmid, Neuenburg (DE)

(73) Assignee: Novartis AG, Basel (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,289

(22) Filed: Apr. 30, 2013

(65) Prior Publication Data

US 2013/0237480 A1    Sep. 12, 2013

Related U.S. Application Data

(62) Division of application No. 12/162,715, filed as application No. PCT/EP2007/001036 on Feb. 7, 2007, now Pat. No. 8,450,272.

(30) Foreign Application Priority Data

Feb. 9, 2006 (GB) .................................. 0602639.7

(51) Int. Cl.
  *A61K 38/31* (2006.01)
  *A61P 5/02* (2006.01)
  *C07K 14/655* (2006.01)

(52) U.S. Cl.
  CPC .............. *A61K 38/31* (2013.01); *C07K 14/655* (2013.01)

(58) Field of Classification Search
  CPC ... A61K 38/31; C07K 14/655; H01H 13/702; H01H 13/785; H01H 2201/028; H01H 2203/05; H01H 2207/008; H01H 2207/01; H01H 2209/014; H01H 2229/016; H01H 2231/004
  See application file for complete search history.

(56) References Cited

U.S. PATENT DOCUMENTS

| | | | |
|---|---|---|---|
| 8,450,272 B2 * | 5/2013 | Schmid ......................... | 514/11.1 |
| 2003/0153494 A1 | 8/2003 | Gordon | |
| 2004/0198653 A1 | 10/2004 | Culler et al. | |
| 2005/0124549 A1 | 6/2005 | Uberti et al. | |

FOREIGN PATENT DOCUMENTS

| | | | | |
|---|---|---|---|---|
| EP | 1787658 A1 * | 10/2005 | ............. | A61K 47/10 |
| WO | 0210192 A2 | 2/2002 | | |
| WO | WO 02/070555 | 9/2002 | ............ | C07K 14/655 |
| WO | WO03/000196 A2 | 1/2003 | | |
| WO | 2005/041901 | 5/2005 | | |

OTHER PUBLICATIONS

Cap et al. Inhibition of Hormone Secretion in GH-Secreting Pituitary Adenomas by Receptor-Subtype Specific Somatostatin Analogues in vitro. Gen. Physiol. Biophys. 2003, vol. 22, pp. 201-212.*
Ren et al. Functionoal Association of Somatostatin Receptor Subtypes 2 and 5 in Inhibiting Human Growth Hormone Secretion. The Journal of Clinical Endocrinology and Metabolism. 2003, Vo. 88, No. 9, pp. 4239-4245.*
Joost van der Hoek et al.: "A single-dose comparison of the actue effects between the new somatostatin analog SOM230 and octreotide in acromegalic patients", The Journal of Clinical Endocrinology & Metabolism vol. 89(2), pp. 638-645, Feb. 2004.
Tulipano et al., "Differential Inhibition of Growth Hormone Secrection by Analogs Selective for Somatostatin Receptor Subtypes 2 and 5 in Human Growth-Hormone-Secreting Adenoma Cells in vitro", Neuroendocrinology, vol. 73, pp. 344-351, (2001).
Ren et al., "Functional Association of Somatostatin Receptor Subtypes 2 and 5 in Inhibiting Human Growth Hormone Secretion", The Journal of Clinical Endocrinology & Metabolism, vol. 88, pp. 4239-4245 (2003).
Moore et al., "Discovery of Iodinated Somatostatin Analogues Selective for hsst2 and hsst5 with Excellent Inhibition of Growth Hormone and Prolactin Release from Rat Pituitary Cells", J. Med. Chem., vol. 48, pp. 6643-6652 (2005).
Bertherat et al., "Somatostatin Receptors 2 and 5 Are the Major Somatostatin Receptors in Insulinomas: An in Vivo and in Vitro Study", The Journal of Clinical Endocrilology & Metabolism, vol. 88, pp. 5353-5360 (2003).
Adams et al., "Somastatin receptors 2 and 5 preferentially expressed in proliferating endothelium", British Journal of Cancer, vol. 92, pp. 1493-1498 (2005).
Schmid H A, et al: "Short- and long-term effects of octreotide and SOM230 on GH, IGF-I, ACTH, corticosterone and ghrelin in rats", Database Medline [Online] US National Library of Medicine (NLM), Bethesda, MD, US 2005, database accession No. NLM16625842; Journal of Endocrinological Investigation 2005, vol. 28, No. 11 Suppl, 2005 pp. 28-35.
Weckbecker G, et al: "SOM230: A New Somatostin Peptidomimetic with Potent Inhibitory Effects on the Growth Hormone/Insulin-Like Growth Factor-I Axis in Rats, Primates and Dogs", Endocrinology, Baltimore, MD, US, vol. 143, No. 10, 2002, pp. 4123-4130.
Ludvigsen et al: "Regulation of insulin and glucagon secretion from rat pancreatic islets in vitro by somatostatin analogues", Regulatory Peptides, Elsevier BV, NL, vol. 138, No. 1, Dec. 19, 2006 pp. 1-9.

* cited by examiner

*Primary Examiner* — Marcela M Cordero Garcia
(74) *Attorney, Agent, or Firm* — Michelle Han (57) ABSTRACT

The present invention relates to a combination of two or more Somatostatin (SRIF) peptidomimetics (also referred to as Somatostatin- or SRIF-analogs) which have different selectivity for the five human somatostatin receptor subtypes, the use of such combination in the treatment of a disease mediated by activation of somatostatin receptors, and to pharmaceutical compositions comprising such a combination.

5 Claims, 4 Drawing Sheets

COMBINATIONS OF SOMATOSTATIN-ANALOGS WITH DIFFERENT SELECTIVITY FOR HUMAN SOMATOSTATIN RECEPTOR SUBTYPES

The present invention relates to a combination of two or more Somatostatin (SRIF) peptidomimetics (also referred to as Somatostatin- or SRIF-analogs) which have different selectivity for the five human somatostatin receptor subtypes SSTR1, SSTR2, SSTR3. SSTR4 and SSTR5 (SSTR1-5), the use of such combination in the treatment of a disease mediated by activation of somatostatin receptors (SSTR1-5), and to pharmaceutical compositions comprising such a combination.

Somatostatin is a tetradecapeptide having the structure

H-Ala-Gly-Cys-Lys-Asn-Phe-Phe-Trp-Lys-Thr-Phe-Thr-Ser-Cys-OH
  1   2   3   4   5   6   7   8   9  10  11  12  13  14

The somatostatin class is a known class of small peptides comprising the naturally occurring somatostatin-14 and analogues having somatostatin related activity, e.g. as disclosed by A. S. Dutta in Small Peptides, Vol. 19, Elsevier (1993). By "somatostatin analog" as used herein is meant any straight-chain or cyclic polypeptide having a structure based on that of the naturally occurring somatostatin-14 wherein one or more amino acid units have been omitted and/or replaced by one or more other amino radical(s) and/or wherein one or more functional groups have been replaced by one or more other functional groups and/or one or more groups have been replaced by one or several other isosteric groups. In general, the term covers all modified derivatives of the native somatostatin-14 which exhibit a somatostatin related activity, e.g. they bind to at least one of the five somatostatin receptor (SSTR), preferably in the nMolar range.

Natural somatostatin binds and activates all 5 somatostatin receptors (SSTR1-5) with nmol efficacy and thus causes its multiple physiological effects.

Most human (neuro-)endocrine tumors express multiple SSTR.

Synthetically available somatostatin analogs differ in their binding affinity to the different somatostatin receptor subtypes and often bind selectively to one or few subtypes with significantly higher affinity.

Somatostatin analogs of particular interest which are predominately targeting SSTR2 comprise the following compounds:

a.

(D)Phe-Cys-Phe-(D)Trp-Lys-Thr-Cys-Thr-ol also known as octreotide
b. (D)Phe-Cys-Tyr-(D)Trp-Lys-Val-Cys-ThrNH$_2$
c. (D)Phe-Cys-Tyr-(D)Trp-Lys-Val-Cys-TrpNH$_2$ also known as vapreotide
d. (D)Trp-Cys-Phe-(D)Trp-Lys-Thr-Cys-ThrNH$_2$
e. (D)Phe-Cys-Phe-(D)Trp-Lys-Thr-Cys-ThrNH$_2$
f. 3-(2-(Naphthyl)-(D)Ala-Cys-Tyr-(D)Trp-Lys-Val-Cys-ThrNH$_2$ also known as lanreotide
g. (D)Phe-Cys-Tyr-(D)Trp-Lys-Val-Cys-β-Nal-NH$_2$
h. 3-(2-naphthyl)-Ala-Cys-Tyr-(D)Trp-Lys-Val-Cys-β-Nal-NH$_2$
i (D)Phe-Cys-β-Nal-(D)Trp-Lys-Val-Cys-Thr-NH$_2$
j. (D)Phe-Cys-Tyr-(D)Trp-Lys-Leu-Cys-Thr-NH$_2$
k. (D)Phe-Cys-Tyr-(D)Trp-Lys-Cys-Thr-NH$_2$.

A preferred Somatostatin analog which is predominately targeting SSTR2 is octreotide.

Somatostatin analogs of particular interest which are predominately targeting SSTR5 have been described e.g. in WO 97/01579. Said somatostatin analogs comprise the amino acid sequence of formula I

$$-(D/L)Trp-Lys-X_1-X_2- \qquad \text{I}$$

wherein $X_1$ is a radical of formula (a) or (b)

wherein $R_1$ is optionally substituted phenyl, wherein the substituent may be halogen, methyl, ethyl, methoxy or ethoxy,

$R_2$ is $-Z_1-CH_2-R_1$, $-CH_2-CO-O-CH_2-R_1$, wherein $Z_1$ is O or S, and $X_2$ is an α-amino acid having an aromatic residue on the side chain, or an amino acid unit selected from Dab, Dpr, Dpm, His, (Bzl)HyPro, cyclohexyl-Ala and t-butyl-Ala, the residue Lys of said sequence corresponding to the residue Lys$^9$ of the native somatostatin-14.

Somatostatin analogs of particular interest which are predominately targeting SSTR5 have also been described e.g. in WO02/10192. Said somatostatin analogs comprise the compound of formula also called cyclo[{4-(NH$_2$—C$_2$H$_4$—NH—CO—O-)Pro}-Phg-DTrp-Lys-Tyr(4-Bzl)-Phe] or pasireotide, as well as diastereoisomers and mixtures thereof, in free form, in salt or complex form or in protected form. Phg means —HN—CH(C$_6$H$_5$)—CO— and Bzl means benzyl.

Compounds which have a very high binding affinity at SSTR5, in addition to their high binding affinity at SSTR1, 2 and 3 like pasireotide, have been shown to have a stronger inhibitory effect on the secretion of several hormones (e.g. GH, GH dependent and GH independent IGF-1 secretion, ACTH, cortisol resp. corticosterone) with less signs of tachyphylaxis compared to compounds which are predominately targeting SSTR2 (and to a lesser extent SSTR5), like octreotide. This offers the possibility that compounds like pasireotide are also active in animals and patients which express mainly SSTR5 and less or no SSTR2 in their hormone secreting tissue or tumor.

The increased potency of pasireotide vs. octreotide has been demonstrated in octreotide resistant acromegaly patients and in patients with primary Cushing's disease, a disease in which octreotide was not effective. The superiority of pasireotide vs. octreotide is also demonstrated in patients suffering from GEP/NET tumors, which became tachyphylactic after prolonged treatment with octreotide and regained functional responsiveness after treatment with pasireotide.

However, compounds which are strongly targeting SSTR5 and less strongly SSTR2, like pasireotide, sometimes show an increase in glucose levels as an unwanted side effect, which has been observed to a lesser extent with compounds which are predominately targeting SSTR2 (and to a lesser extent SSTR5), like octreotide.

The hyperglycemic effect of pasireotide is dose dependent, whereas even high doses of octreotide may not increase plasma glucose. This means that the simultaneous activation of SSTR2 by pasireotide is not sufficient to reverse the hyperglycemia induced via the activation of SSTR5. Likewise, the simultaneous activation of the SSTR5 by octreotide is not sufficient to induce hyperglycemia.

It was now surprisingly found that a combination of compounds which are predominately targeting SSTR5 with compounds which are predominately targeting SSTR2 still keeps a strong inhibitory effect on hormone secretion (e.g. OH and IGF-I plasma level) while showing no or a significantly reduced hyperglycemic side effect. This synergistic effect permits usage of higher doses of compounds which are predominately targeting SSTR5 in such combinations by limiting their hyperglycemic side effects. One could also increase the efficacy of compounds which are predominately targeting SSTR5 and compounds which are predominately targeting SSTR2 without increasing hyperglycemic effects or use lower doses of both, compounds which are predominately targeting SSTR5 and compounds which are predominately targeting SSTR2 and still have good efficacy.

Figure 1:
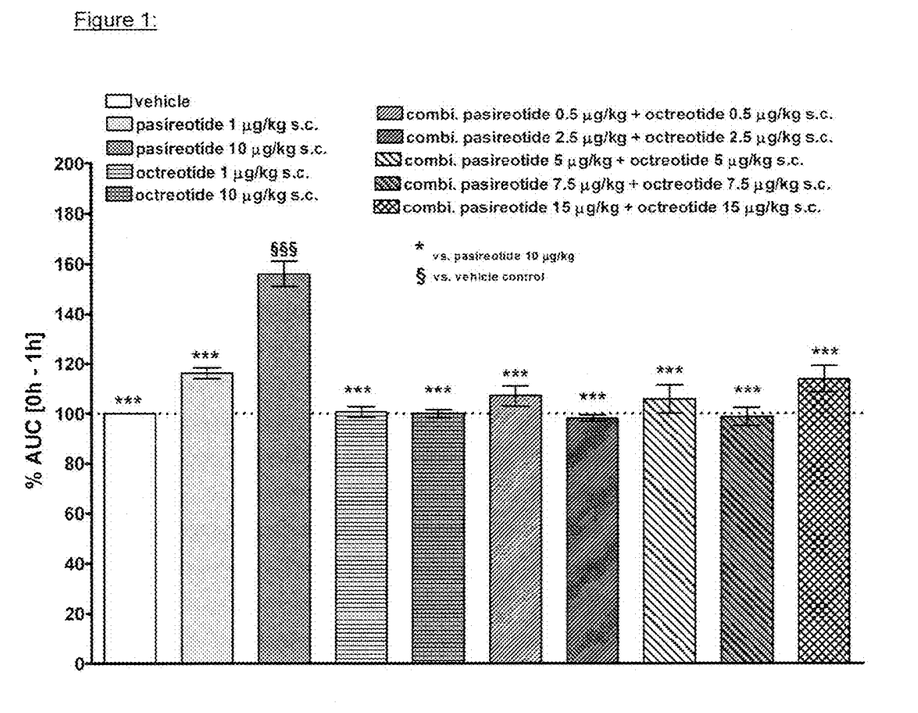
FIG. 1: Acute Effect on Plasma Glucose Level

As shown in FIG. 1, 10 µg/kg pasireotide increased AUC glucose levels by 56% vs. control within 1 hours after the injection. In contrast, the same dose of octreotide had no effect on this parameter. The combination of both substances at 0.5, 2.5, 5, 7.5 and 15 µg/kg each changed AUC glucose levels only by 7, −2, 6, −1 and 14% respectively. This result demonstrates that combination of pasireotide and octreotide results in a smaller or even no increase in glucose than pasireotide alone.

Due to the known pharmacokinetic differences of octreotide ($t_{1/2}$=90 min) and pasireotide ($t_{1/2}$=11 h), a comparison of the effects of both compounds is most relevant within the first hour after the application (Schmid and Silva, 2005, J. Endocrine. Invest. 28:28-35).

In additional experiments it could be demonstrated that even a 50% and 66% lower dose of octreotide could prevent the hyperglycemia induced by 10 and 30 µg/kg pasireotide, respectively within 1 h after the application.

Figure 2:
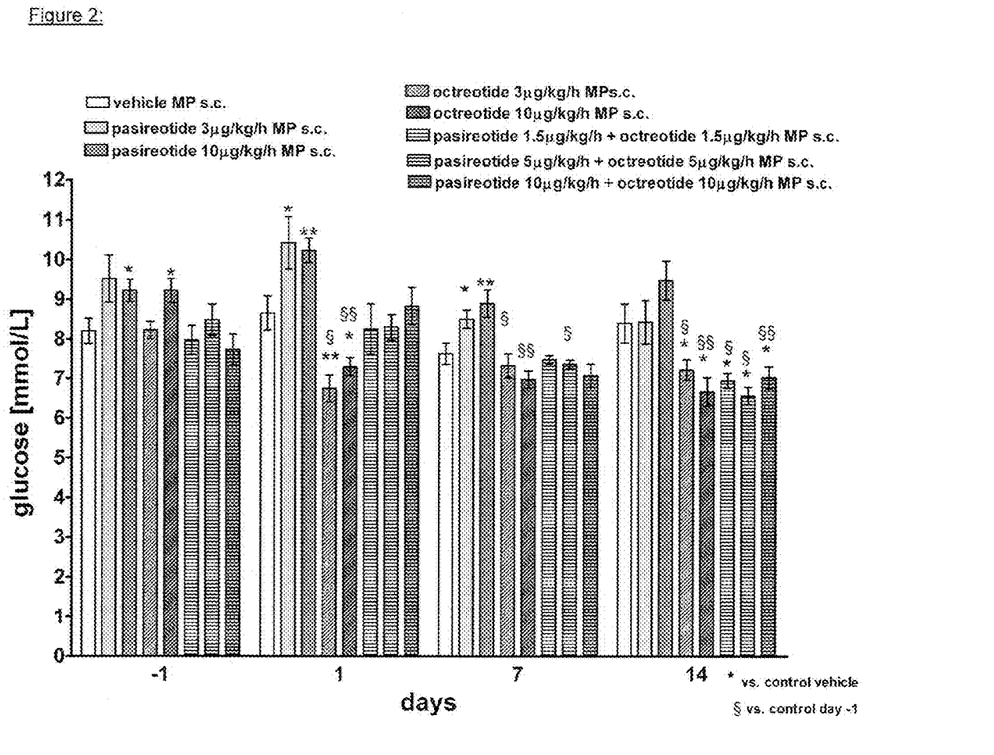
FIG. 2: Long Term Effect on Plasma Glucose Concentration

In order to investigate the efficacy of both compounds together pasireotide and octreotide (3 and 10 µg/kg/h) alone and various combinations (1.5, 5 and 10 µg/kg/h) were permanently infused for 14 days. During long term treatment with 3 and 10 µg/kg/h pasireotide alone, the plasma level of glucose are slightly, but significantly increased on day 1 and 7 of treatment (FIG. 2). In contrast, octreotide had no effect or caused a small but significant reduction in plasma glucose. Surprisingly, combined application of 1.5, 5 and 10 µg/kg/h octreotide and pasireotide did not increase plasma glucose and the levels in all combination groups were indistinguishable from the groups treated with octreotide for 7 and 14 days.

Figure 3:
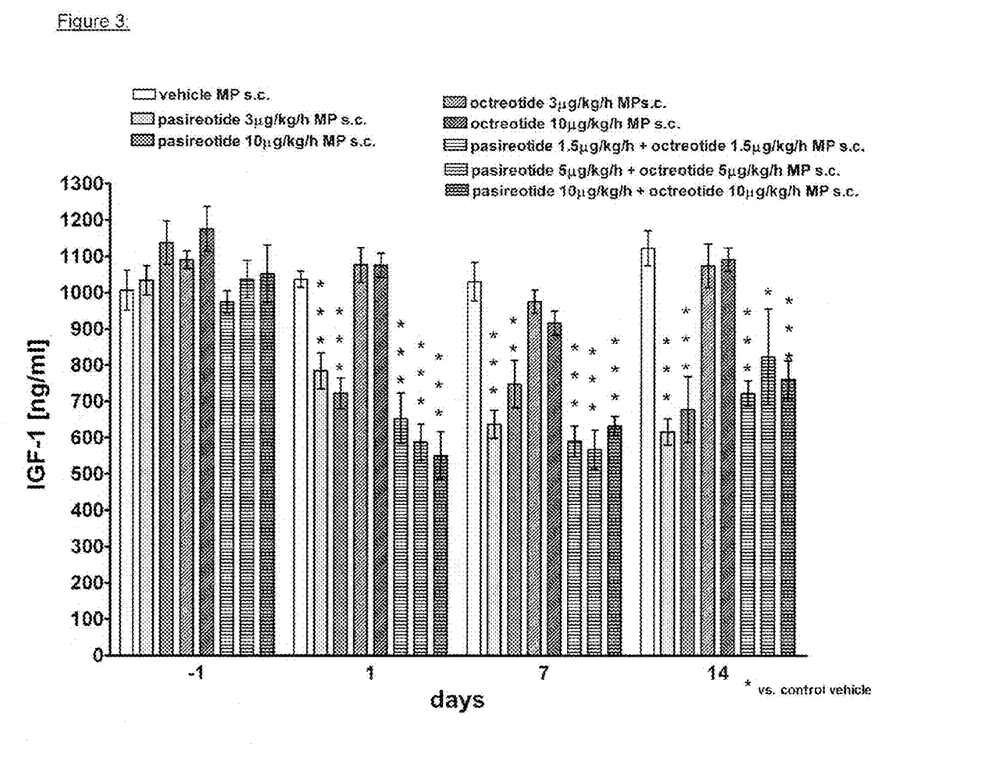
FIG. 3: Long Term Effect on IGF-1 Plasma Levels
Figure 4:
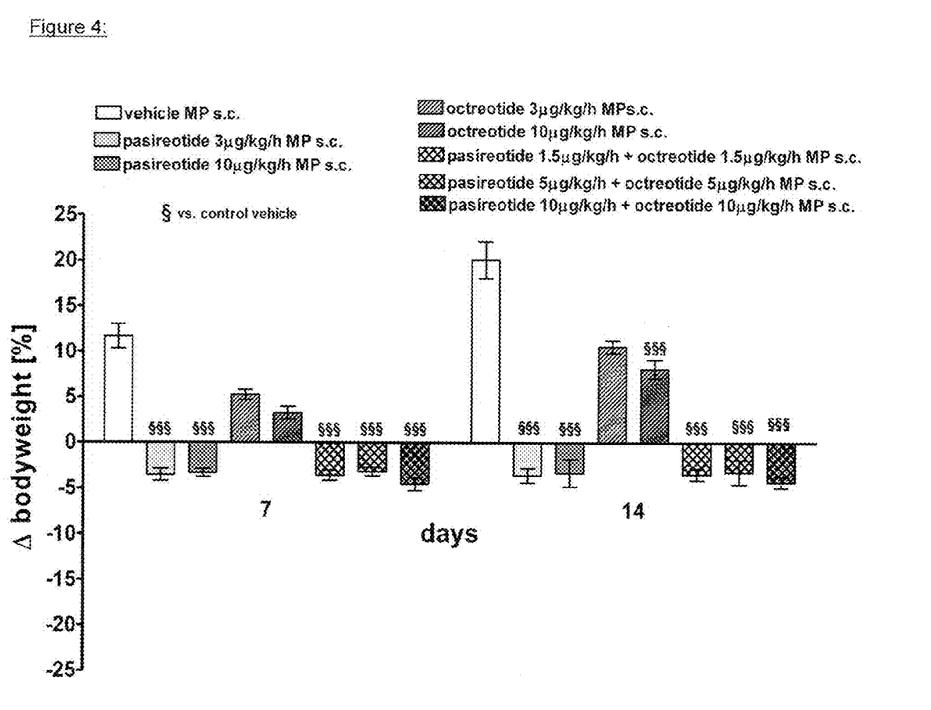
FIG. 4: Long Term Effect on Body Weight

For pharmaceutical use, the unexpected finding of a reduction in glucose after combined application of octreotide and pasireotide is most relevant if this combination does not reduce the potency of the single agents. The data on IGF-1 level and body weight clearly demonstrate that the combination of 50% lower doses showed the same potency as the high doses applied individually (FIG. 3 and FIG. 4). Unexpectedly, the combination of even 7-fold lower doses of both compounds (1.5 µg/kg/h) applied simultaneously showed the same potency on IGF-1 (FIG. 3) and body weight (FIG. 4) as the maximum dose of pasireotide tested in this experiment (10 µg/kg/h). Pharmacologically even more relevant might be the finding that the combined application of the same dose 10 µg/kg/h or even a 50% lower dose of each compound resulted in a significantly stronger inhibition of IGF-1 on day 1 than 10 µg/kg/h of pasireotide alone.

In summary these results indicate that combination of these two compounds not only increases their potency (based on IGF-1 level), but in addition the combination also reduces the negative hyperglycemic side effect caused by pasireotide.

SHORT DESCRIPTION OF THE FIGURES

Effect of an acute s.c. injection of octreotide and pasireotide in rats (1 and 10 µg/kg) and different combinations thereof on the accumulated glucose levels between 0 and 1 hour after the injection (n=6 animals per group).

* indicate statistical significance vs. pasireotide 10 µg/kg and § indicate statistical significance vs. vehicle control.

Effect of long term application of octreotide and pasireotide alone and in combination on plasma glucose concentration in rats. Compounds were continuously infused by osmotic minipumps at 3 and 10 µg/kg/h for the single compounds and at 1.5, 5 and 10 µg/kg/h for the combinations. Plasma glucose levels were determined one day before and 1, 7 and 14 days after minipumps implantation.

§ and * indicate statistical significance vs. day −1 and vs. the vehicle control on the same day, respectively.

Effect of long term application of octreotide and pasireotide alone and in combination on IGF-1 plasma levels in rats. Compounds were continuously infused by osmotic minipumps at 3 and 10 µg/kg/h for the single compounds and at 1.5, 5 and 10 µg/kg/h for the combinations. IGF-1 plasma glucose levels were determined one day before and 1, 7 and 14 days after minipumps implantation.

* indicate statistical significance vs. the vehicle control on the same day

Effect of long term application of octreotide and pasireotide alone and in combination on body weight in rats. Compounds were continuously infused by osmotic minipumps at 3 and 10 µg/kg/h for the single compounds and at 1.5, 5 and 10 µg/kg/h for the combinations. Body weight of rats is expressed as % change in BW after 7 and 14 days of treatment compared with the body weight on the day before minipumps implantation.

In a further aspect, the present invention relates to a combination comprising at least two different Somatostatin (SRIF) analogs wherein one SRIF-analog is predominately targeting SSTR2 and another SRIF-analog is predominately targeting SSTR5 (hereinafter referred to as COMBINATION OF THE INVENTION), the use of such combination in the treatment of a disease mediated by activation of somatostatin receptors (SSTR1-5), and to pharmaceutical compositions comprising a COMBINATION OF THE INVENTION.

The term "SRIF-analog predominately targeting SSTR2" as used herein refers to compounds which have a high binding affinity to SSTR2, preferentially an IC50<1 nmol/l, variable affinities to SSTR1, 3 and 4 and a binding affinity to SSTR5 which is at least 5-fold, preferentially 10-fold, lower than the affinity to SSTR2, and includes, but is not limited to octreotide or lanreotide. The preferred SRIF-analog predominately targeting SSTR2 is octreotide.

The term "SRIF-analog predominately targeting SSTR5" as used herein refers to compounds which have a high binding affinity to SSTR5, preferentially an IC50<1 nmol/l, variable affinities to SSTR1, 3 and 4 and a binding affinity to SSTR2 which is at least 2-fold lower than the affinity to SSTR5, and includes, but is not limited to pasireotide (Schmid at al., Neuroendocrinol. 2004; 80:47-50).

The term "a disease mediated by activation of somatostatin receptors (SSTR1-5)" as used herein includes, but is not limited to disorders with an aetiology comprising or associated with excess GH-secretion and/or excess of IGF-1 e.g. treatment of acromegaly as well as treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, hyper- and hypoglycemia, e.g. morbid obesity or hypothalamic or hyperinsulinemic obesity, enterocutaneous and pancreaticocutaneous fistula, irritable bowel syndrome, inflammatory diseases, e.g. Grave's Disease, inflammatory bowel disease, psoriasis or rheumatoid arthritis, polycystic kidney disease, dumping syndrome, watery diarrhea syndrome, AIDS-related diarrhea, chemotherapy- or radiation-induced diarrhea, acute or chronic pancreatitis and gastrointestinal hormone secreting tumors (e.g. GEP tumors, for example vipomas, glucagonomas, insulinomas carcinoids and the like), lymphocyte malignancies, e.g. lymphomas or leukemias, hepatocellular carcinoma, gastrointestinal bleeding. e.g. variceal oesophagial bleeding, sleep apnoe, grelinoma, Prader-Willi-syndrome.

It can be shown by established test models that the COMBINATION OF THE INVENTION results in an effective prevention or, preferably, treatment of a disease mediated by activation of somatostatin receptors (SSTR1-5). Especially the SRIF-analogues predominantly targeting SSTR5 can now be used at effective doses without or with only reduced hyperglycemic side effects when administering them in a COMBINATION OF THE INVENTION.

The person skilled in the pertinent art is fully enabled to select a relevant test model to prove the hereinbefore and hereinafter indicated therapeutic indications and beneficial effects. The pharmacological activity may, for example, be demonstrated in clinical studies in patients with a disease mediated by activation of somatostatin receptors (SSTR1-5) similar to those described for octreotide or pasireotide.

In accordance with the particular findings of the invention, the present invention also provides a treating of a disease mediated by activation of somatostatin receptors (SSTR1-5) in a warm-blooded animal in need thereof comprising administering to the animal a COMBINATION OF THE INVENTION in a quantity which is jointly therapeutically effective against a disease mediated by activation of somatostatin receptors (SSTR1-5) and in which the compounds can also be present in the form of their pharmaceutically acceptable salts.

The present invention relates also to a pharmaceutical composition comprising a quantity, which is jointly therapeutically effective against a disease mediated by activation of somatostatin receptors (SSTR1-5), of a COMBINATION OF THE INVENTION and at least one pharmaceutically acceptable carrier.

The present invention relates also to the use of a COMBINATION OF THE INVENTION for the preparation of a medicament for the treatment of a disease mediated by activation of somatostatin receptors (SSTR1-5).

The present invention relates also to a commercial package comprising a COMBINATION OF THE INVENTION together with instructions for simultaneous, separate or sequential use thereof in the treatment of a disease mediated by activation of somatostatin receptors (SSTR1-5).

Somatostatin analogs may be administered in free form or in pharmaceutically acceptable salt form. Such salts may be prepared in conventional manner and exhibit the same order of activity as the free compound.

Pharmaceutical compositions for the treatment of a disease mediated by activation of somatostatin receptors (SSTR1-5) comprise an effective amount of the Somatostatin analog in free base form or in pharmaceutically acceptable salt form together with one or more pharmaceutically acceptable diluent or carrier. Such compositions may be formulated in conventional manner Somatostatin analogs may also be administered in sustained release form, e.g. in the form of implants, microcapsules, microspheres or nanospheres comprising e.g. a biodegradable polymer or copolymer, in the form of a liposomal formulation, or in the form of an autogel, e.g. a solid or semi-solid composition capable of forming a gel after interaction with patient's body fluids.

The COMPOUNDS OF THE INVENTION can, for example, be formulated as disclosed in U.S. Pat. No. 5,538,739 (especially octreotide) or WO05/046645 (especially pasireotide).

Somatostatin analogs or a pharmaceutically acceptable salt thereof may be administered by any conventional route, for example parenterally e.g. in form of injectable solutions or suspensions (including e.g. the sustained release form as indicated above), orally using a conventional absorption enhancer if necessary, in a nasal or a suppository form or topically, e.g. in the form of an ophthalmic liquid, gel, ointment or suspension preparation, e.g. a liposomal, microsphere or nanosphere formulation, e.g. for instillation or subconjunctival or intra- or pen-ocular injections.

The present pharmaceutical compositions are prepared in a manner known per se, and comprise approximately from 1% to 100%, preferentially from approximately 1% to 40%, especially from approximately 20% to 30%, active ingredient.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, expression of SSTR, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutical effect in a non-effective dosage of one or both of the first and second active ingredient, and especially a strong synergism the first and second active ingredient.

In particular, a therapeutically effective amount of each of the active ingredients of the COMBINATION OF THE INVENTION may be administered simultaneously or sequentially and in any order, and the components may be administered separately or as a fixed combination. For example, the method of treatment of diseases according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in viva to the active ingredient. The instant invention is therefore to be understood as embracing all such regimes of simultaneous or alternating treatment and the term "administering" is to be interpreted accordingly.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

The results disclosed herein indicate that a combination which comprises a COMBINATION OF THE INVENTION achieves an improved therapeutic effect compared to either compound alone in the treatment of a disease mediated by activation of somatostatin receptors (SSTR1-5). One particular benefit of the COMBINATION OF THE INVENTION is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated.

The pharmacological activity of a COMBINATION OF THE INVENTION may, for example, also be demonstrated in clinical studies. Such clinical studies are preferably randomized, double-blind, clinical studies in patients having a disease mediated by activation of somatostatin receptors (SSTR1-5). Such studies demonstrate, in particular, the synergism of the active ingredients of the COMBINATION OF THE INVENTION. The studies are, in particular, suitable to compare the effects of a monotherapy using the active ingredients and a COMBINATION OF THE INVENTION.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, ameliorate or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

The following examples serve to illustrate the invention without limiting the invention in its scope.

Introduction

Based on previous experiments in rats it was known that acute injection of pasireotide causes an increase in glucose, which was rapid in onset (within 30 min after injection), reached its peak between 1 and 3 h and returned to baseline values after 6-8 h. Repeated or long term injections of pasireotide in rats resulted in strong tachyphylaxis. Therefore only moderate increases in glucose have been observed after repeated or long-term treatment with pasireotide mainly on the first day(s) of treatment. Based on these data it was expected that short term experiments were optimally suited to examine the effect of octreotide and pasireotide and their combination on plasma glucose. In order to investigate the efficacy of both compounds and their combination on a relevant parameter in rats plasma GH and IGF-1 levels as well as body weight were determined in rats within 14 days of continuous infusion with the compounds. GH and IGF-1 levels are elevated in acromegaly patients and can be effectively reduced in about 60 percent of all patients by octreotide treatment. Due to the known pulsatile release pattern of GH and the low sensitivity of the available GH RIA, levels of IGF-1 and body weight (BW) are more reliable parameters to determine efficacy of a compound on the GH/IGF-1 system. GH and IGF-1 are both growth factors which are responsible for growth of animals and humans and lack of these factors result in growth retardation in animals which are still growing (like in rats). Therefore BW in combination with IGF-1 measurement is an additional relevant parameter to demonstrate efficacy of somatostatin analogues. Unlike the rapid changes in glucose levels, changes in IGF-1 levels are only observed after 1-2 days of treatment with somatostatin analogues.

Methods:

In order to investigate the effects of a combination of pasireotide and octreotide on efficacy and plasma glucose the following short-term and long-term experiments were performed in adult male Lewis rats (250-300 g).

In the short term experiment octreotide and pasireotide and their combination were s.c. injected in rats in 1 ml saline. Blood samples were taken by sublingual bleeding the rats 15 min, 30 min, 1 h, 3 h, 6 h and 8 h after the injection and blood glucose was determined using ACCU-Chek Compact (Roche), which was newly calibrated before each measurement. In order to determine the overall effect of the treatment on glucose the area under the curve (AUC) was determined using GraphPad Prizm. 4.0.

In the long-term experiments octreotide and pasireotide and their combination were s.c. infused in rats using osmotic minipumps (Alzet model: 2002). Blood samples were taken by sublingual bleeding on the day before minipump implantation and after 1, 7 and 14 days, Glucose was determined using ACCU-Chek Compact (Rhoche) and IGF-1 levels using commercial ELISA (octeia rat IGF-1 from Immunediagnostics, UK).

What is claimed is:

1. A combination comprising at least two different Somatostatin (SRIF) analogs wherein one SRIF-analog is predominately targeting SSTR2 and is octreotide, and another SRIF-analog is predominately targeting SSTR5 and is pasireotide in which the active ingredients are present in each case in free form or in the form of a pharmaceutically acceptable salt and optionally at least one pharmaceutically acceptable carrier; for simultaneous, separate or sequential use.

2. Combination according to claim 1 which is a combined preparation or a pharmaceutical composition.

3. Method of treating a disorder with an aetiology comprising or associated with excess GH-secretion and/or excess of IGF-1 in a warm-blooded animal in need thereof comprising administering to the animal a combination according to claim 1 in a quantity which is jointly therapeutically effective a disorder with an aetiology comprising or associated with excess GH-secretion and/or excess of IGF-1 and in which the compounds can also be present in the form of their pharmaceutically acceptable salts.

4. A pharmaceutical composition comprising a quantity, which is jointly therapeutically effective against a disorder with an aetiology comprising or associated with excess GH-secretion and/or excess of IGF-1, of a combination according to claim 1 and at least one pharmaceutically acceptable carrier.

5. A method according to claim 3 wherein the disorder is acromegaly, type I or type II diabetes mellitus, diabetic proliferative retinopathy, diabetic macular edema, nephropathy, neuropathy, dawn phenomenon, and other metabolic disorders related to insulin or glucagon release, obesity, hyper- and hypoglycemia, morbid obesity or hypothalamic or hyperinsulinemic obesity, enterocutaneous and pancreaticocutaneous fistula, irritable bowel syndrome, inflammatory diseases, Grave's Disease, inflammatory bowel disease, psoriasis or rheumatoid arthritis, polycystic kidney disease, dumping syndrome, watery diarrhea syndrome, AIDS-related diarrhea, chemotherapy- or radiation-induced diarrhea, acute or chronic pancreatitis and gastrointestinal hormone secreting tumors, GEP tumors, vipomas, glucagonomas, insulinomas carcinoids, lymphocyte malignancies, lymphomas, leukemias, hepatocellular carcinoma, gastrointestinal bleeding, variceal oesophagial bleeding, sleep apnoe, grelinoma or PraderWilli syndrome.

* * * * *

UNITED STATES PATENT AND TRADEMARK OFFICE
CERTIFICATE OF CORRECTION

| | | |
|---|---|---|
| PATENT NO. | : 9,149,510 B2 | Page 1 of 1 |
| APPLICATION NO. | : 13/873289 | |
| DATED | : October 6, 2015 | |
| INVENTOR(S) | : Herbert Schmid | |

It is certified that error appears in the above-identified patent and that said Letters Patent is hereby corrected as shown below:

Specification

Column 3, line 67, change "e.g. OH" to -- "e.g. GH" --.

Signed and Sealed this
Twenty-second Day of March, 2016

Michelle K. Lee
*Director of the United States Patent and Trademark Office*